United States Patent [19]

Morinaga et al.

[11] Patent Number: 4,673,749

[45] Date of Patent: Jun. 16, 1987

[54] PROCESS FOR PRODUCING AN INDOLINE

[75] Inventors: Michio Morinaga; Akira Ikeda; Akira Shinohara, all of Shimizu, Japan

[73] Assignee: Ihara Chemical Industry Co., Ltd., Tokyo, Japan

[21] Appl. No.: 731,393

[22] Filed: May 7, 1985

[30] Foreign Application Priority Data

May 10, 1984 [JP] Japan .................. 59-93677

[51] Int. Cl.⁴ ................ C07D 209/08; C07D 209/12; C07D 209/14
[52] U.S. Cl. .................... 548/490; 548/491
[58] Field of Search ................ 548/490, 491

[56] References Cited

U.S. PATENT DOCUMENTS 4,087,442  5/1978  Nakayama et al. ............. 548/490
4,159,271  6/1979  Sano et al. ..................... 548/490
4,280,958  7/1981  Nakayama et al. ............. 548/490

FOREIGN PATENT DOCUMENTS 2804263  2/1978  Fed. Rep. of Germany .
1498579  10/1976  United Kingdom .
2033392  10/1979  United Kingdom .

OTHER PUBLICATIONS

Ohara, Chemical Abstracts 97:127280z (1982).
Patent Abstracts of Japan, vol. 6, No. 3, Jan. 9, 1982, p. (C-86) (881), JP-A-56-128756, (Sendai Fukusoka Kagaku Kenkyusho) 08-10-1981.

Primary Examiner—Donald G. Daus
Assistant Examiner—Mary E. Ceperley
Attorney, Agent, or Firm—Oblon, Fisher, Spivak, McClelland & Maier

[57] ABSTRACT

A process for producing an indoline of the formula:

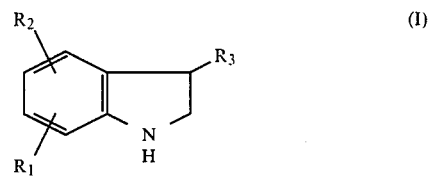

wherein $R_1$ is a hydrogen atom, a lower alkyl group, a lower alkoxy group, a nitro group or a hydroxyl group, $R_2$ is a hydrogen atom, a lower alkoxy group or a nitro group, and $R_3$ is a hydrogen atom, a lower alkyl group or a substituted lower alkyl group, by a cyclization reaction of a 2-halogenophenethylamine of the formula:

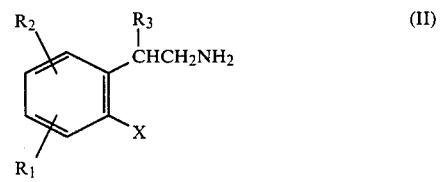

wherein $R_1$, $R_2$ and $R_3$ are as defined above, and X is a halogen atom, in the presence of a copper type catalyst and a dehydrohalogenating agent, characterized in that copper bis(8-hydroxyquinolinolate) is used as the copper type catalyst, and an alkali is used as the dehydrohalogenating agent.

7 Claims, No Drawings

PROCESS FOR PRODUCING AN INDOLINE

The present invention relates to a process for producing indolines which are useful as intermediates for the production of agricultural chemicals, etc. or as intermediates for the production of indoles useful as starting materials for agricultural chemicals, medicines, perfumes or dystuffs.

For the production of indolines by a cyclization reaction of 2-halogenophenethylamines in the presence of a copper type catalyst and a dehydrohalogenating agent, there has been known a process wherein metal copper, an inorganic copper compound such as copper chloride, copper sulfate, copper nitrate or copper oxide, or an organic copper compound such as copper acetate or copper oxalate is used as the copper type catalyst, and ammonia is used as the dehydrohalogenating agent (U.S. Pat. Nos. 4,087,442 and 4,159,271), or a method wherein metal copper, an inorganic copper compound such as copper chloride, copper sulfate, copper nitrate or copper hydroxide, or an organic copper compound such as copper oxalate or copper acetate is used as the copper type catalyst, and an amine such as monoethanolamine, diethanolamine or triethylamine is used as the dehydrohalogenating agent (U.S. Pat. No. 4,280,958).

In the prior art process wherein the copper type catalyst and ammonia are used, the reaction is required to be conducted in a closed pressure reactor under a pressurized condition because of the use of ammonia, the reactor is required to be corrosion resistant, since ammonia and an aqueous solution of ammonium halide formed as a by-product are corrosive, and the load for the waste water treatment increases as the ammonium halide is water-soluble and enters into the waste water. Thus, this process have difficulties for an industrial process for the production of indolines by the cyclization reaction of 2-halogenophenethylamines.

In the process wherein the cyclization reaction is conducted in the presence of a copper type catalyst and an amine, the amine used as the dehydrohalogenating agent is expensive, and accordingly the amine is required to be recovered after the reaction and reused for a practical industrial operation. Thus, the reaction solution will have to be subjected to liquid separation, and then the aqueous layer containing the amine and the amine salt will have to be neutralized and freed by sodium hydroxide, followed by water-removal and filtration treatments for the recovery of the amine. Thus, in addition to the step for the preparation of the indoline, additional steps for the recovery of the amine will be amine will be required, and the amine is water-soluble, whereby the recovery rate is poor. Further, it is difficult to separate the amine so as to prevent it from entering into the indoline. Furthermore, the load for the waste water treatment increases as the amine is involved in the waste water, and a substantial installation will be required also for this waste water treatment. Thus, this process also has difficulties for an industrial process for the production of indolines by the cyclization reaction of 2-halogenophenethylamines.

The present inventors have conducted extensive researches to solve the difficulties of the conventional techniques and to develop an industrial process for the production of indolines, and have finally found that the conventional problems can be solved by using copper bis(8-hydroxyquinolinolate) (hereinafter referred to simply as "quinoline copper") as the copper type catalyst and an alkali as the dehydrohalogenating agent in a process for the production of indolines by the cyclization reaction of 2-halogenophenethylamines in the presence of the copper type catalyst and the dehydrohalogenating agent. The present invention has been accomplished based on this discovery.

Namely, the present invention provides a process for producing an indoline of the formula:

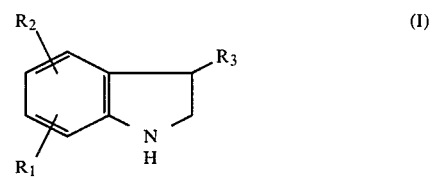

wherein $R_1$ is a hydrogen atom, a lower alkyl group, a lower alkoxy group, a nitro group or a hydroxyl group, $R_2$ is a hydrogen atom, a lower alkoxy group or a nitro group, and $R_3$ is a hydrogen atom, a lower alkyl group or a substituted lower alkyl group, by a cyclization reaction of a 2-halogenophenethylamine of the formula:

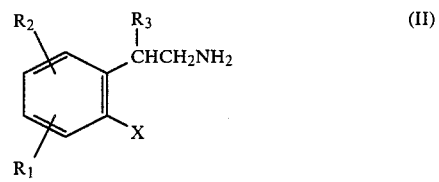

wherein $R_1$, $R_2$ and $R_3$ are as defined above, and X is a halogen atom, in the presence of a copper type catalyst and a dehydrohalogenating agent, characterized in that copper bis(8-hydroxyquinolinolate) is used as the copper type catalyst, and an alkali is used as the dehydrohalogenating agent.

Now, the present invention will be described in detail with reference to the preferred embodiments.

The reaction of the present invention is represented by the following formulas.

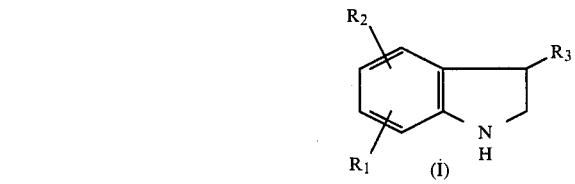

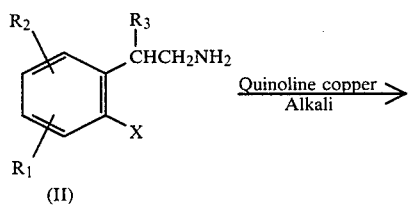

In the above formulas, $R_1$, $R_2$, $R_3$ and X are as defined above.

In the 2-halogenophenethylamine of the formula II used in the process of the present invention, substituent $R_1$ on the benzene ring is a hydrogen atom; a lower alkyl group such as methyl, ethyl, propyl, isopropyl, butyl or isobutyl; a lower alkoxy group such as methoxy, ethoxy or propoxy; a nitro group; or a hydroxyl group; $R_2$ is a hydrogen atom; a lower alkoxy group such as methoxy, ethoxy, propoxy, isopropoxy or butoxy; or a nitro group; $R_3$ is a hydrogen atom; a lower alkyl group such as methyl, ethyl, propyl, isopropyl, butyl or isobutyl; or a lower alkyl group substituted by hydroxyl, amino, nitrile or alkoxy; and X is a halogen atom such as fluorine, chlorine, bromine or iodine. Specifically, the 2-halogenophenethylamines of the formula II include, for instance, 2-chlorophenethylamine, 2-chloro-β-methylphenethylamine, 2-bromo-β-methylphenethylamine, 2-bromo-β-ethylphenethylamine, 2-bromo-β-isopropylphenethylamine, 2-chloro-β-butylphenethylamine, 2-chloro-5-ethylphenethylamine, 2-chloro-5-isopropylphenethylamine, 2-bromo-5-butylphenethylamine, 2-chloro-4-methyl-β-butylphenethylamine, 2-bromo-4-ethyl-β-ethylphenethylamine, 2-bromo-4-isopropyl-5-isopropoxyphenethylamine, 2-chloro-4-methyl-5-isopropoxy-β-methylphenethylamine, 2-fluoro-4-methyl-5-nitrophenethylamine, 2-chloro-4-butyl-5-nitro-β-methylphenethylamine, 2-chloro-4-methoxyphenethylamine, 2-bromo-4-isopropoxyphenethylamine, 2-bromo-4-ethoxy-3-ethylphenethylamine, 2-chloro-4,5-dimethoxyphenethylamine, 2-chloro-4,5-diisopropoxy-β-methylphenethylamine, 2-bromo-4-isopropoxy-5-nitrophenethylamine, 2-iodo-4-nitrophenethylamine, 2-fluoro-2-nitro-β-isopropylphenethylamine, 2-bromo-4-nitro-5-methoxy-β-ethylphenethylamine, 2-bromo-3,5-dinitrophenethylamine, 2-bromo-3,5-dinitro-β-ethylphenethylamine, 2-chloro-4-hydroxyphenethylamine, 2-fluoro-4-hydroxyphenethylamine, 2-chloro-4-hydroxy-3-ethoxyphenethylamine, 2-chloro-4-hydroxy-5-methoxyphenethylamine, 2-chloro-4-hydroxy-5-isopropoxy-β-isopropylphenethylamine, 2-chloro-4-hydroxy-5-nitrophenethylamine, 2-bromo-4-hydroxy-5-nitro-β-ethylphenethylamine, β-hydroxymethyl-2-chlorophenethylamine, β-aminomethyl-2-chlorophenethylamine, β-(2-N,N-dimethylaminoethyl)-2-chlorophenethylamine, β-cyanomethyl-2-chlorophenethylamine, β-(2,2-diethoxyethyl)-2-chlorophenethylamine, and β-(1,3-dioxolan-2-yl)methyl-2-chlorophenethylamine.

The alkali used in the process of the present invention may be a hydroxide or carbonate of an alkali metal or alkaline earth metal. For instance, there may be mentioned sodium hydroxide, potassium hydroxide, calcium hydroxide, magnesium hydroxide, lithium hydroxide, sodium carbonate, potassium carbonate and calcium carbonate. These alkalis may be used in the form of a solution or suspension in water. It is preferred to use them in the form of an aqueous solution. This alkali is used usually in an amount of at least the stoichiometric amount, preferably from 1.1 to 3 equivalents, as the dehydrohalogenating agent, relative to the 2-halogenophenethylamine.

The quinoline copper used as a catalyst in the process of the present invention is copper bis(8-hydroxyquinolinolate). If the conventional copper type catalyst, for example, metal copper, an inorganic copper compound such as copper chloride, or an organic copper compound such as copper oxalate is used as the catalyst, the reaction does not proceed. The quinoline copper may be used as such, or may be formed in the reaction system by adding a copper salt and quinoline to the reaction system. The quinoline copper is used in an amount within a range of from 0.01 to 20 mol % preferably from 0.1 to 10 mol %, per mol of the 2-halogenophenethylamine.

The reaction of the present invention is carried out by charging the phenethylamine, the alkali and the quinoline copper into a reactor and heating and stirring the mixture. The reaction temperature is not higher than the refluxing temperature of the reaction mixture, preferably from 50 to 120° C. The reaction of the process of the present invention is usually conducted under atmospheric pressure, but may be conducted under pressure. The reaction time is preferably from 1 to 20 hours. The reaction may be conducted in an inert gas atmosphere. After the reaction, the reaction mixture obtained is subjected to liquid separation, and the aqueous layer comprising an alkali halide as a by-product and water, is separated. The organic layer comprising the formed indoline and the quinoline copper, is washed with water and then with an acid, followed by concentration and distillation to obtain the desired indoline. The catalyst quinoline copper remains in the still residue after the distillation of the indoline, and can be recovered by filtration after an addition of a solvent such as toluene. Otherwise, it may also be recovered by precipitating it by cooling the reaction mixture before the liquid separation, followed by filtration.

According to the present invention, as opposed to the conventional processes, it is not necessary to recover the dehydrohalogenating agent, the alkali can readily be separated from the indoline, the indoline can be isolated in high purity by distillation, and there is no adverse effect to the waste water. Further, the quinoline copper used as the catalyst can readily be recovered by a conventional method, and can be used repeatedly. Thus, according to the present invention, indolines can be produced in good yield at low cost in an industrial operation.

Now, the present invention will be described in further detail with reference to Examples. However, it should be understood that the invention is by no means restricted to these specific Examples.

EXAMPLE 1

Into a 100 ml reaction flask equipped with a condenser, a thermometer and a stirrer, 15.56 g (0.1 mol) of 2-chlorophenethylamine, 22.0 g (0.11 mol) of a 20% sodium hydroxide aqueous solution and 0.176 g (0.5 mol %) of quinoline copper were charged, and reacted at 110° C. for 8 hours. The reaction mixture thereby obtained was subjected to liquid separation to separate the aqueous layer from the organic layer. The organic layer was washed with an acid and distilled to obtain 11.4 g of indoline (boiling point: 94°–95° C./11 mmHg). The purity was 99.5%, and the yield was 96%.

EXAMPLES 2 to 8

The operation was conducted in the same manner as in Example 1 except that the temperature, the amount of quinoline copper and the alkali were changed as shown in Table 1. The results thereby obtained are shown in Table 1.

TABLE 1

| | | | | Indoline | |
|---|---|---|---|---|---|
| | Catalyst (mol %) | Temp. (°C.) | Alkali (mol) | Amount (g) | Yield (%) |
| 2 | 1.76 g (5.0) | 110 | NaOH (0.11) | 11.4 g | 96.0% |
| 3 | 0.036 g (0.1) | 110 | NaOH (0.11) | 11.2 g | 94.0% |
| 4 | 0.35 g (1.0) | 90 | NaOH (0.11) | 11.3 g | 95.0% |

TABLE 1-continued

| | Catalyst (mol %) | Temp. (°C.) | Alkali (mol) | Indoline Amount (g) | Yield (%) |
|---|---|---|---|---|---|
| 5 | 0.35 g (1.0) | 110 | NaOH (0.11) | 11.2 g | 94.0% |
| 6 | 0.35 g (1.0) | 110 | KOH (0.11) | 11.4 g | 96.0% |
| 7 | 0.35 g (1.0) | 110 | Ca(OH)$_2$ (0.055) | 11.3 g | 95.0% |
| 8 | 0.35 g (1.0) | 110 | K$_2$CO$_3$ (0.11) | 11.3 g | 95.0% |

Note: In Table 1, as the alkali, a 20% aqueous solution was used with respect to NaOH and K$_2$CO$_3$, and the same amount of water as in Example 1 was used with respect to Ca(OH)$_2$.

EXAMPLE 9

The reaction was conducted in the same manner as in Example 1 except that the quinoline copper recovered from the still residue in Example 1 was reused, whereby 11.4 g of indoline was obtained. The yield was 96.0%. Further, it was possible to reuse the catalyst.

EXAMPLES 10 to 21

The operation was conducted in the same manner as in Example 1 except that the type of the 2-halogenophenethylamine was changed as shown in Table 2. The results are shown in Table 2.

TABLE 2

| | 2-Halogenophenethylamines | Indolines Chemical Name | Physical properties | Yield (%) |
|---|---|---|---|---|
| 10 | 2-Chloro-β-methylphenethylamine | 3-Methylindoline | b.p. 67–69° C./ 0.45 mmHg | 96 |
| 11 | 2-Chloro-5-ethylphenethylamine | 5-Ethylindoline | b.p. 110–111° C./ 7 mmHg | 95 |
| 12 | 2-Bromo-5-ethyl-β-ethylphenethylamine | 3,5-Diethylindoline | b.p. 87–92° C./ 3 mmHg | 95 |
| 13 | 2-Bromo-5-n-butylphenethylamine | 5-n-Butylindoline | b.p. 90–95° C./ 5 mmHg | 95 |
| 14 | 2-Chloro-4-methoxyphenethylamine | 6-Methoxyindoline | b.p. 145–146° C./ 15 mmHg | 95 |
| 15 | 2-Bromo-5-nitro-4-i-propoxyphenethylamine | 5-Nitro-6-iso-propoxyindoline | m.p. 200–202° C. | 94 |
| 16 | 2-Chloro-4,5-dimethoxydiphenethylamine | 5,6-Dimethoxyindoline | m.p. 108.5° C. | 94 |
| 17 | 2-Chloro-5-nitrophenethylamine | 5-Nitroindoline | m.p. 65–66° C. | 95 |
| 18 | 2-Fluoro-4-hydroxyphenethylamine | 6-Hydroxyindoline | m.p. 118–119° C. | 95 |
| 19 | 2-Bromo-β-ethylphenethylamine | 3-Ethylindoline | b.p. 109–110° C./ 7 mmHg | 96 |
| 20 | 2-Chloro-β-isopropylphenethylamine | 3-Isopropylindoline | b.p. 72–75° C./ 0.9 mmHg | 96 |
| 21 | 2-Chloro-β-butylphenethylamine | 3-Butylindoline | b.p. 87–88° C./ 3 mmHg | 96 |

COMPARATIVE EXAMPLES 1 and 2

The reaction was conducted in the same manner as in Example 1 except that instead of quinoline copper, 0.226 g (1 mol %) of copper oxalate (Comparative Example 1) or 0.134 g (1 mol %) of copper chloride (Comparative Example 2) was used, whereby the reaction did not proceed.

As is evident from the Examples and Comparative Examples, according to the present invention, indolines having a high purity can readily be obtained in good yield under normal pressure by using quinoline copper as the copper type catalyst and an alkali as the dehydrohalogenating agent in the process for the production of indolines by the cyclization reaction of 2-halogenophenethylamines in the presence of the copper type catalyst and the dehydrohalogenating agent. Further, since an alkali is used as the dehydrohalogenating agent, indolines can readily be isolated, and there is no adverse effect to the waste water. The quinoline copper used as the catalyst can be recovered by a conventional method, and can be used repeatedly. Thus, the process of the present invention is very useful as an industrial process for the production of indolines.

We claim:

1. A process for producing an indoline of the formula:

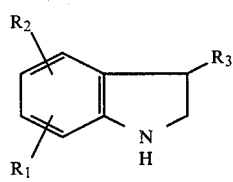

(I)

wherein R$_1$ is a hydrogen atom, a lower alkyl group, a lower alkoxy group, a nitro group or a hydroxyl group, R$_2$ is a hydrogen atom, a lower alkoxy group or a nitro group, and R$_3$ is a hydrogen atom, a lower alkyl group or a lower alkyl group substituted by hydroxyl, amino, nitrile or alkoxy, by a cyclization reaction of a 2-halogenophenethylamine of the formula:

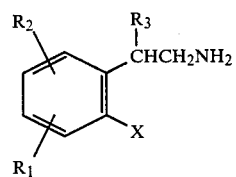

(II)

wherein R$_1$, R$_2$ and R$_3$ are as defined above, and X is a halogen atom, in the presence of a copper type catalyst and a dehydrohalogenating agent, characterized in that copper bis(8-hydroxyquinolinolate) is used as the copper type catalyst, and an aqueous alkali is used as the dehydrohalogenating agent.

2. The process according to claim 1, wherein the alkali is a hydroxide or carbonate of an alkali metal or alkaline earth metal.

3. The process according to claim 1, wherein the alkali is selected from the group consisting of sodium hydroxide, potassium hydroxide, calcium hydroxide, magnesium hydroxide, lithium hydroxide, sodium carbonate, potassium carbonate and calcium carbonate.

4. The process according to claim 1, wherein the alkali is used in an amount of at least the stoichiometric amount, as the dehydrohalogenating agent, relative to the 2-halogenophenethylamine.

5. The process according to claim 1, wherein the alkali is used in an amount of from 1.1 to 3.0 equivalents relative to the 2-halogenophenethylamine.

6. The process according to claim 1, wherein copper bis(8-hydroxyquinolinolate) is used in an amount of from 0.01 to 20 mol % per mol of the 2-halogenophenethylamine.

7. The process according to claim 1, wherein copper bis(8-hydroxyquinolinolate) is used in an amount of from 0.1 to 10 mol % per mol of the 2-halogenophenethylamine.

* * * * *